United States Patent
Araújo et al.

(10) Patent No.: US 11,634,159 B2
(45) Date of Patent: Apr. 25, 2023

(54) DETERMINING AN UNDESIRED ACTION OF A VEHICLE

(71) Applicant: Telefonaktiebolaget LM Ericsson (publ), Stockholm (SE)

(72) Inventors: José Araújo, Stockholm (SE); Soma Tayamon, Stockholm (SE)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 295 days.

(21) Appl. No.: 16/769,730

(22) PCT Filed: Dec. 8, 2017

(86) PCT No.: PCT/SE2017/051235
§ 371 (c)(1),
(2) Date: Jun. 4, 2020

(87) PCT Pub. No.: WO2019/112501
PCT Pub. Date: Jun. 13, 2019

(65) Prior Publication Data
US 2020/0346665 A1 Nov. 5, 2020

(51) Int. Cl.
*B60W 60/00* (2020.01)
*A61B 5/16* (2006.01)
(Continued)

(52) U.S. Cl.
CPC ......... *B60W 60/0016* (2020.02); *A61B 5/163* (2017.08); *A61B 5/168* (2013.01);
(Continued)

(58) Field of Classification Search
CPC . B60W 60/0016; B60W 30/025; B60K 31/00; B60K 35/00; A61B 5/16;
(Continued)

(56) References Cited

U.S. PATENT DOCUMENTS

2012/0212353 A1* 8/2012 Fung ............... B60W 10/18
701/1
2014/0347265 A1* 11/2014 Aimone ............... A61B 5/163
345/156
(Continued)

FOREIGN PATENT DOCUMENTS

EP 3239011 A1 11/2017
JP 2004220348 A 8/2004
(Continued)

OTHER PUBLICATIONS

Welke, Dominik, et al., "Brain Responses During Robot-Error Observation," ArXiv, published Aug. 4, 2017, URL: "https://arxiv.org/ftp/arxiv/papers/1708/1708.01465.pdf", 11 pages.
(Continued)

*Primary Examiner* — Yuri Kan
(74) *Attorney, Agent, or Firm* — Withrow & Terranova, PLLC (57) ABSTRACT

It is presented a method performed in a vehicle action determiner for determining an undesired action of a first vehicle and a resulting action. The method comprises: detecting that a first user is focusing on the first vehicle; acquiring brain activity data of the first user; determining a negative reaction of the first user based on the brain activity data; determining when the first vehicle is performing an undesired action based on the first user focusing on the first vehicle and the negative reaction of the first user; determining the resulting action taken by an autonomous vehicle, based on the first vehicle performing the undesired action; and triggering the autonomous vehicle to perform the resulting action.

19 Claims, 5 Drawing Sheets

(51) Int. Cl.
*A61B 5/18* (2006.01)
*B60W 30/09* (2012.01)
*B60W 30/095* (2012.01)
*B60W 40/08* (2012.01)
*G06F 3/01* (2006.01)
*G08G 1/16* (2006.01)
*A61B 5/369* (2021.01)

(52) U.S. Cl.
CPC .............. *A61B 5/18* (2013.01); *A61B 5/369* (2021.01); *B60W 30/09* (2013.01); *B60W 30/0956* (2013.01); *B60W 40/08* (2013.01); *G06F 3/013* (2013.01); *G06F 3/015* (2013.01); *G08G 1/162* (2013.01); *B60W 2540/22* (2013.01); *B60W 2540/225* (2020.02); *B60W 2554/80* (2020.02)

(58) Field of Classification Search
CPC ........ A61B 7/04; A61B 5/163; G06V 20/597; B60R 11/04
See application file for complete search history.

(56) References Cited

U.S. PATENT DOCUMENTS

| | | | | |
|---|---|---|---|---|
| 2014/0348389 | A1* | 11/2014 | Graumann | G06V 20/597 382/104 |
| 2015/0099946 | A1* | 4/2015 | Sahin | A61B 7/04 600/301 |
| 2015/0223731 | A1* | 8/2015 | Sahin | A61B 5/16 600/595 |
| 2016/0107509 | A1* | 4/2016 | Kirsch | B60W 40/08 165/202 |
| 2016/0152180 | A1 | 6/2016 | Kirsch et al. | |
| 2016/0167672 | A1* | 6/2016 | Krueger | G16H 40/63 340/576 |
| 2017/0135621 | A1 | 5/2017 | Lee et al. | |
| 2017/0225677 | A1* | 8/2017 | Yoshida | B60W 30/025 |
| 2017/0303842 | A1 | 10/2017 | Yoshida et al. | |

FOREIGN PATENT DOCUMENTS

| | | | | |
|---|---|---|---|---|
| JP | 2011198247 | A | * 10/2011 | ............ B60R 11/04 |
| JP | 2016052881 | A | 4/2016 | |
| JP | 2017204015 | A | * 11/2017 | ............ B60K 31/00 |
| WO | 2017177128 | A1 | 10/2017 | |

OTHER PUBLICATIONS

International Search Report and Written Opinion for International Patent Application No. PCT/SE2017/051235, dated Aug. 27, 2018, 10 pages.
Extended European Search Report for European Patent Application No. 17934216.7, dated Nov. 17, 2020, 8 pages.
Notice of Reasons for Rejection for Japanese Patent Application No. 2020-531033, dated Oct. 12, 2021, 10 pages.
Notice of Reasons for Rejection for Japanese Patent Application No. 2020-531033, dated Aug. 30, 2022, 13 pages.

* cited by examiner

DETERMINING AN UNDESIRED ACTION OF A VEHICLE

This application is a 35 U.S.C. § 371 national phase filing of International Application No. PCT/SE2017/051235, filed Dec. 8, 2017, the disclosure of which is incorporated herein by reference in its entirety.

TECHNICAL FIELD

The invention relates to a method, vehicle action determiners, a computer program and a computer program product for determining an undesired action of a vehicle.

BACKGROUND

There is a great deal of research and development currently in the field of vehicles with autonomous propulsion capability. Applications range from passenger transport such as bus and taxi services, to goods transports performed by heavy-duty vehicles. In recent years, many companies have validated their autonomous heavy-duty vehicles in real roads. The Google driverless car has been operating in several areas in the United States since 2012. In 2014, Google reported that their cars have completed a total of 1.1 million km in autonomous mode in California. Furthermore, aerial vehicles, such as drones, can be autonomous vehicles.

Machine learning is used in many autonomous vehicles to improve driving capability over time. The performance of such a machine learning model benefits from both quantity and quality of feedback. However, the quantity of feedback is always limited and any new sources of feedback would greatly benefit the performance of machine learning based driving.

SUMMARY

It is an object of embodiments presented herein to provide an improved feedback to autonomous vehicles based on vehicles performing undesired actions.

According to a first aspect, it is presented a method for determining an undesired action of a first vehicle and a resulting action. The method is performed in a vehicle action determiner and comprises the steps of: detecting user focus, by detecting that a first user is focusing on the first vehicle; acquiring brain activity data of the first user; determining a negative reaction of the first user based on the brain activity data; determining when the first vehicle is performing an undesired action based on the first user focusing on the first vehicle and the negative reaction of the first user; determining the resulting action to be taken by an autonomous vehicle, based on the first vehicle performing the undesired action; and triggering the autonomous vehicle to perform the resulting action.

The steps of detecting user focus, acquiring brain activity data may be repeated for a second user. In such a case, the step of determining when the first vehicle is performing an undesired action is further based on the second user focusing on the first vehicle and a negative reaction of the second user.

The method may further comprise the step of: acquiring control parameters of the first vehicle. In such a case, the step of determining when the first vehicle is performing an undesired action is further based on the control parameters of the first vehicle.

The control parameters may comprise at least one parameter describing a current motion of the first vehicle.

The control parameters may comprise at least one parameter relating to road characteristics of a road driven by the first vehicle.

The step of determining a resulting action may comprise considering control parameters of the first vehicle.

The step of detecting user focus may be based on gaze tracking.

In the step of acquiring brain activity data, the brain activity data may be based on electroencephalography, EEG.

The step of detecting user focus may comprise only considering first vehicles within a specific distance from the first user.

The step of determining when the first vehicle is performing an undesired action may further be based on a current geographic location of the first vehicle.

The step of determining when the first vehicle is performing an undesired action may further be based on historic driving data of the first vehicle.

In the step of determining a resulting action, the resulting action may be a corrective control action of the autonomous vehicle.

The method may further comprise the step of: providing, when the first vehicle is not performing an undesired action, feedback to the first user, indicating that the first vehicle is not performing an undesired action.

According to a second aspect, it is presented a vehicle action determiner for determining an undesired action of a first vehicle and a resulting action. The vehicle action determiner comprises: a processor; and a memory storing instructions that, when executed by the processor, cause the vehicle action determiner to: detect user focus, by detecting that a first user is focusing on the first vehicle; acquire brain activity data of the first user; determine a negative reaction of the first user based on the brain activity data; determine when the first vehicle is performing an undesired action based on the first user focusing on the first vehicle and the negative reaction of the first user; determine a resulting action to be taken by an autonomous vehicle, based on the first vehicle performing the undesired action; and trigger the autonomous vehicle to perform the resulting action.

The instructions to detect user focus, acquire brain activity data may be repeated for a second user. In such a case, the instructions to determine when the first vehicle is performing an undesired action may further be based on the second user focusing on the first vehicle and a negative reaction of the second user.

The vehicle action determiner may further comprise instructions that, when executed by the processor, cause the vehicle action determiner to: acquire control parameters of the first vehicle. In such a case, the instructions to determine when the first vehicle is performing an undesired action is further based on the control parameters of the first vehicle.

The control parameters may comprise at least one parameter describing a current motion of the first vehicle.

The control parameters may comprise at least one parameter relating to road characteristics of a road driven by the first vehicle.

The instructions to determine a resulting action may comprise instructions that, when executed by the processor, cause the vehicle action determiner to consider control parameters of the first vehicle.

The instructions to detect may comprise instructions that, when executed by the processor, cause the vehicle action determiner to detect user focus based on gaze tracking.

In the instructions to acquire brain activity data, the brain activity data may be based on electroencephalography, EEG.

The instructions to detect user focus may comprise instructions that, when executed by the processor, cause the vehicle action determiner to only consider first vehicles within a specific distance from the first user.

The instructions to determine when the first vehicle is performing an undesired action may comprise instructions that, when executed by the processor, cause the vehicle action determiner to determine that the first vehicle is performing an undesired action further based on a current geographic location of the first vehicle.

The instructions to determine when the first vehicle is performing an undesired action may comprise instructions that, when executed by the processor, cause the vehicle action determiner to determine when the first vehicle is performing an undesired action further based on historic driving data of the first vehicle.

In the instructions to determine a resulting action, the resulting action may be a corrective control action of the autonomous vehicle.

The vehicle action determiner may further comprise instructions that, when executed by the processor, cause the vehicle action determiner to provide, when the first vehicle is not performing an undesired action, feedback to the first user, indicating that the first vehicle is not performing an undesired action.

According to a third aspect, it is presented a vehicle action determiner comprising: means for detecting user focus, by detecting that a first user is focusing on a first vehicle; means for acquiring brain activity data of the first user; means for determining a negative reaction of the first user based on the brain activity data; means for determining when the first vehicle is performing an undesired action based on the first user focusing on the first vehicle and the negative reaction of the first user; means for determining the resulting action to be taken by an autonomous vehicle, based on the first vehicle performing the undesired action; and means for triggering the autonomous vehicle to perform the resulting action.

According to a fourth aspect, it is presented a computer program for determining an undesired action of a first vehicle and a resulting action. The computer program comprises computer program code which, when run on a vehicle action determiner causes the vehicle action determiner to: detect user focus, by detecting that a first user is focusing on the first vehicle; acquire brain activity data of the first user; determine a negative reaction of the first user based on the brain activity data; determine when the first vehicle is performing an undesired action based on the first user focusing on the first vehicle and the negative reaction of the first user; determine the resulting action to be taken by an autonomous vehicle, based on the first vehicle performing the undesired action; and trigger the autonomous vehicle to perform the resulting action.

According to a fifth aspect, it is presented a computer program product comprising a computer program according to the fourth aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

Embodiments presented herein are based on the realisation that the reaction of users can be utilised to provide feedback on vehicle actions. Specifically, the feedback is based on detecting brain activity data from a user to find out when the user has a negative reaction. This is coupled to an vehicle being the focus of the user to thereby provide negative feedback for an autonomous vehicle to learn from that situation. Since the feedback is based on brain sensing, the user does not need to provide any feedback using a user interface, whereby the system can work without user input to a mass large amounts of very valuable feedback data for the performance of autonomous vehicles.

Figure 1A:
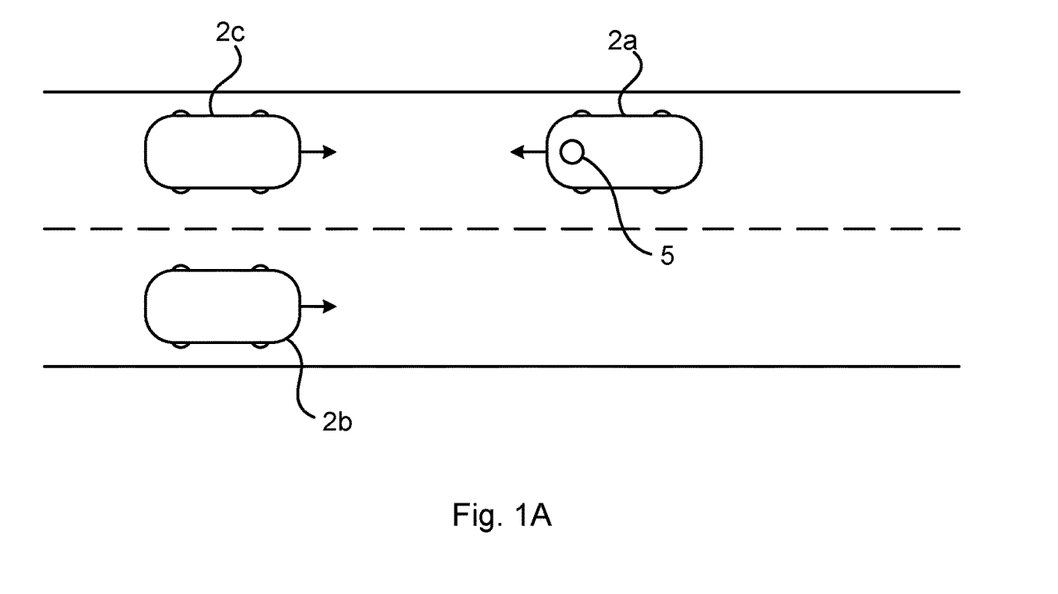
FIGS. 1A-B are schematic drawings illustrating an environment in which embodiments presented herein can be applied.
Figure 1B:
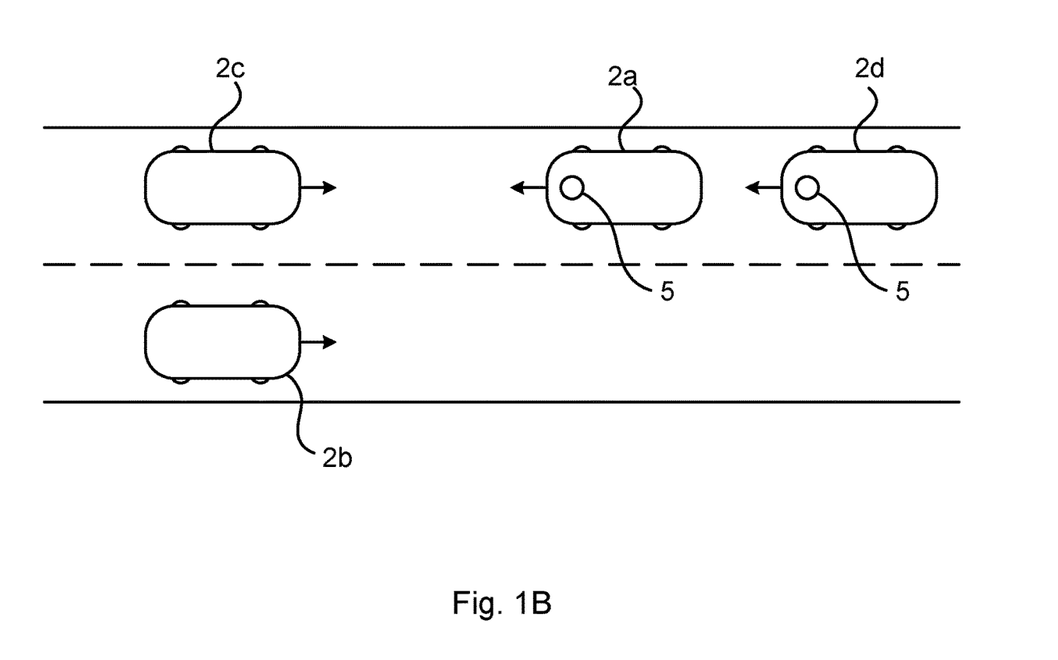

FIGS. 1A-B are schematic drawings illustrating an environment in which embodiments presented herein can be applied. There are here four vehicles 2a-d (of which three are shown in FIG. 1A). At least the first vehicle 2a and the fourth vehicle 2d are autonomous vehicles, being capable of autonomous propulsion for at least part of the time. The second vehicle 2b and the third vehicle 2c can also be autonomous vehicles or can be humanly controlled vehicles. For instance, the autonomous vehicles can be a car with autonomous driving capability or an aerial vehicle (e.g. a drone) with autonomous flight capability. The autonomous vehicles comprise one or more cameras and other sensors which are used to analyse the environment of the vehicle and control the vehicle accordingly. The control of the vehicle can be based on a machine learning model. The machine learning model can be improved by feeding appropriate feedback to the model, including resulting actions. The more feedback that is available to train the machine learning model, the better the performance. In other words, each instance of a specific set of features as input (e.g. one or more of the control parameters mentioned below) and a known output, such as a resulting action determined from an undesired action, can be used to train the machine learning model further. When such combinations of inputs and outputs a mass in large numbers, as is made possible by embodiments presented herein since no user interaction is needed, this results in continuous improvement of the machine learning model. The vehicles 2a-c can also comprise additional sensors for acquiring control parameters which are relevant for controlling the vehicle such as audio, vehicle motion, vehicle speed, road conditions, aerial route conditions etc. The vehicles 2a-c can also acquire external control parameters such as traffic conditions, road accidents/construction zones, weather conditions, etc. by communicating with neighbouring vehicles and/or a server. The vehicles 2a-c contain a control unit which defines how the vehicle should be operated in autonomous mode, e.g. based on the machine learning model.

In the scenarios herein, the local regulations stipulate right hand traffic. In the scenario of FIG. 1A, a user 5 is travelling in the first autonomous vehicle 2a. A second autonomous vehicle 2b is travelling in the opposite direction. However, a third vehicle 2C is overtaking the second autonomous vehicle 2b, in a way that is dangerous for the first autonomous vehicle 2a and thus the user 5. The third vehicle 2c can be an autonomous vehicle or a traditional, human controlled vehicle. According to embodiments presented herein, the user 5 will notice the action of the autonomous vehicle 2c and a brain activity acquirer will capture data from the brain of the user 5 from which it can be deduced that the user 5 has a negative reaction. A negative reaction is a negative emotional reaction of the user than can be detected. When human observe other humans committing errors, their brains show a specific activation pattern in response to these errors, which can e.g. reflect feelings such as fear, anger, disgust, etc. This will be used to allow the system to learn from the situation and will reduce the risk of autonomous vehicles acting in the same way as the third vehicle 2c in this scenario.

In FIG. 1B, a scenario is shown where the user 5 of a fourth autonomous vehicle 2d also notices the undesired action of the third vehicle 2c, giving more weight to the situation.

Figure 2A:
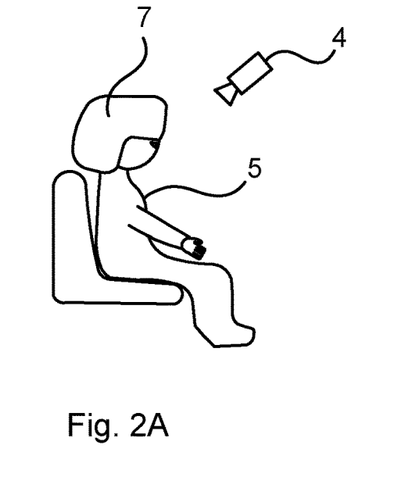
FIGS. 2A-B are schematic drawings illustrating brain activity sensing according to two embodiments which can be applied in the environment of FIGS. 1A-B.
Figure 2B:
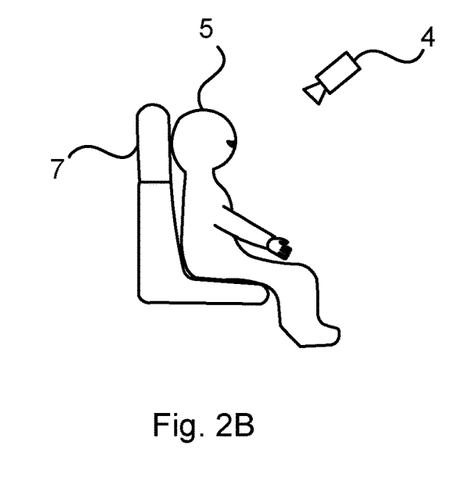

FIGS. 2A-B are schematic drawings illustrating brain activity sensing according to two embodiments which can be applied in the environment of FIGS. 1A-B.

In FIG. 2A, the user 5 is shown sitting in a seat of an autonomous vehicle, e.g. the first autonomous vehicle 2a of FIGS. 1A-B. The user is wearing a brain activity acquirer 7 in the form of a head mounted sensor arrangement. A camera 4 is directed towards the eyes of the user to allow gaze tracking, as known in the art per se. Using gaze tracking, it can be determined where the user 5 is looking, e.g. at a specific vehicle.

Looking now to the brain sensor device 7. Brain sensor devices, also known as brain computer interfaces (BCI) are devices that are capable of measuring the brain activity of a user, typically through Electroencephalography (EEG). These brain sensor devices 7 can be in the form of an externally mounted head mounted device, an outer-ear or inner-ear mounted device which may be considered wearable brain sensor devices 7. A brain sensor device 7 could also be an embedded device in the user head.

The brain sensor device 7 can be used to detect various aspects of user brain activity. One such activity is to detect when a user experiences a negative reaction. Compared to other visionary uses of brain activity detection, the negative reaction detection is much more straightforward and feasible using data provided by the brain sensor devices 7 available today. For instance, it is disclosed in Welke et al: "Brain Responses During Robot-Error Observation", available at https://arxiv.org/ftp/arxiv/papers/1708/1708.01465.pdf at the time of filing this application, how EEG is used to differentiate when a person observes a correct vs erroneous action of a robot.

In FIG. 2B, the brain sensor device 7 is implemented as part of a headrest of the seat of the user 5. In this way, no device needs to be worn by the user.

Figure 3:
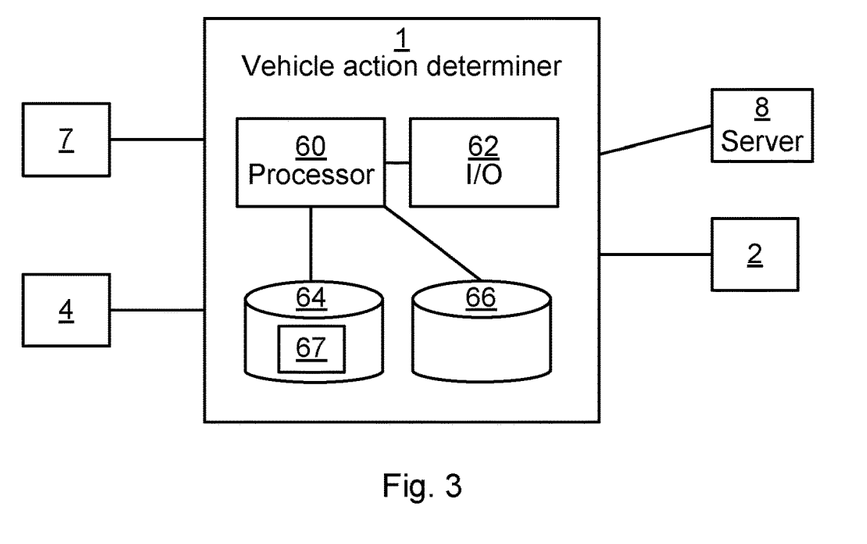
FIG. 3 is a schematic diagram illustrating components of a vehicle action determiner that can be used in the environment of FIGS. 1A-B.

FIG. 3 is a schematic diagram illustrating components of a vehicle action determiner 1 that can be used in the environment of FIGS. 1A-B. When the vehicle action determiner is implemented as part of a host device (see FIGS. 4A-C and description below), one or more of these components can be shared with the host device. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIGS. 5A-C below.

The memory 64 can be any combination of random access memory (RAM) and read only memory (ROM). The memory 64 also comprises persistent, i.e. non transitory, storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random access memory (RAM) and read only memory (ROM).

The vehicle action determiner 1 further comprises an I/O interface 62 for communicating with other external entities. Optionally, the I/O interface 62 further includes a user interface.

Other components of the vehicle action determiner 1 are omitted in order not to obscure the concepts presented herein.

The vehicle action determiner 1 can connect to a brain sensor device 7, which can be any of the brain sensor devices 7 of FIGS. 2A-B, respectively. The vehicle action determiner 1 can also connect to a server 8.

Moreover, the vehicle action determiner 1 can connect to an autonomous vehicle 2, which may be an autonomous vehicle in which the user is travelling. The vehicle action determiner 1 can also connect to a camera 4 to allow gaze tracking of the user.

Figure 4A:
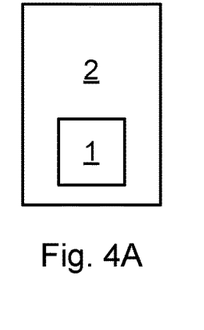
FIGS. 4A-D are schematic diagrams illustrating embodiments of how the vehicle action determiner of FIG. 3 can be implemented.
Figure 4B:
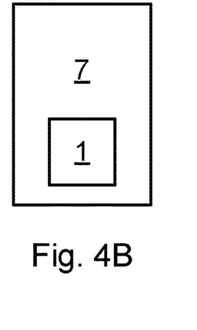
Figure 4C:
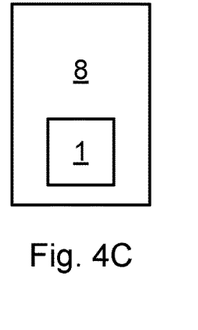

FIGS. 4A-D are schematic diagrams illustrating embodiments of how the vehicle action determiner 1 of FIG. 3 can be implemented. The vehicle action determiner 1 can be implemented as a stand-alone device or it can form part of a host device, as shown in FIGS. 4A-C.

In FIG. 4A, the vehicle action determiner 1 is shown as implemented in the autonomous vehicle 2. The autonomous vehicle 2 is thus the host device for the vehicle action determiner 1. In this case, the autonomous vehicle can be, but does not need to be, the autonomous vehicle in which the user is travelling at the moment.

In FIG. 4B, the vehicle action determiner 1 is shown as implemented in the brain sensor device 7. The brain sensor device 7 is thus the host device for the vehicle action determiner 1. In this embodiment, the brain sensor device acquires brain data of a user being anywhere where the focus of the user can be detected. For instance, the user can be situated by the side of the road with external cameras used to detect user focus. Alternatively, the brain sensor device also comprises a camera to detect eye gaze of the user. The brain sensor device 7 then uses the brain data of the user and eye gaze of the user to determine whether an undesired of an observed vehicle occurs.

In FIG. 4C, the vehicle action determiner 1 is shown as implemented in the server 8. The server 8 is thus the host device for the vehicle action determiner 1. In this embodiment, the server 8 can be connected to a brain activity acquirer for acquiring brain data of a user being anywhere where the focus of the user can be detected. For instance, the user can be situated by the side of the road with external cameras used to detect user focus. The server then uses the brain data of the user and eye gaze of the user to determine whether an undesired of an observed vehicle occurs.

Figure 4D:
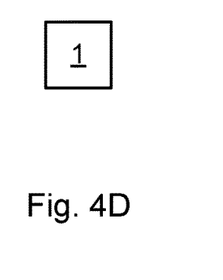

In FIG. 4D, the vehicle action determiner 1 is shown implemented as a stand-alone device. In this embodiment, there is no host device for the vehicle action determiner 1.

Figure 5A:
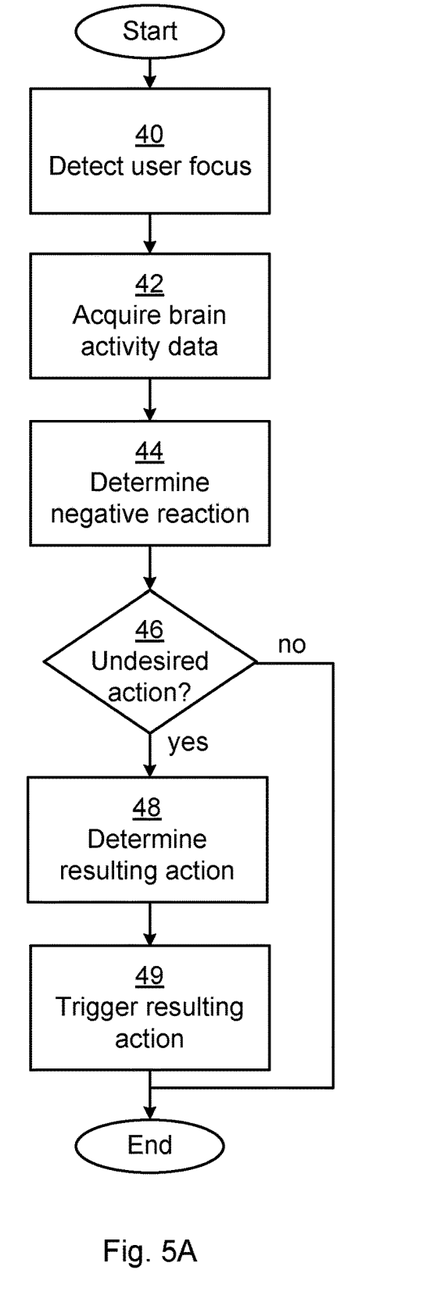
FIGS. 5A-C are flow charts illustrating methods for determining an undesired action of a first vehicle and a resulting action, the method being performed in the vehicle action determiner of FIG. 3.
Figure 5B:
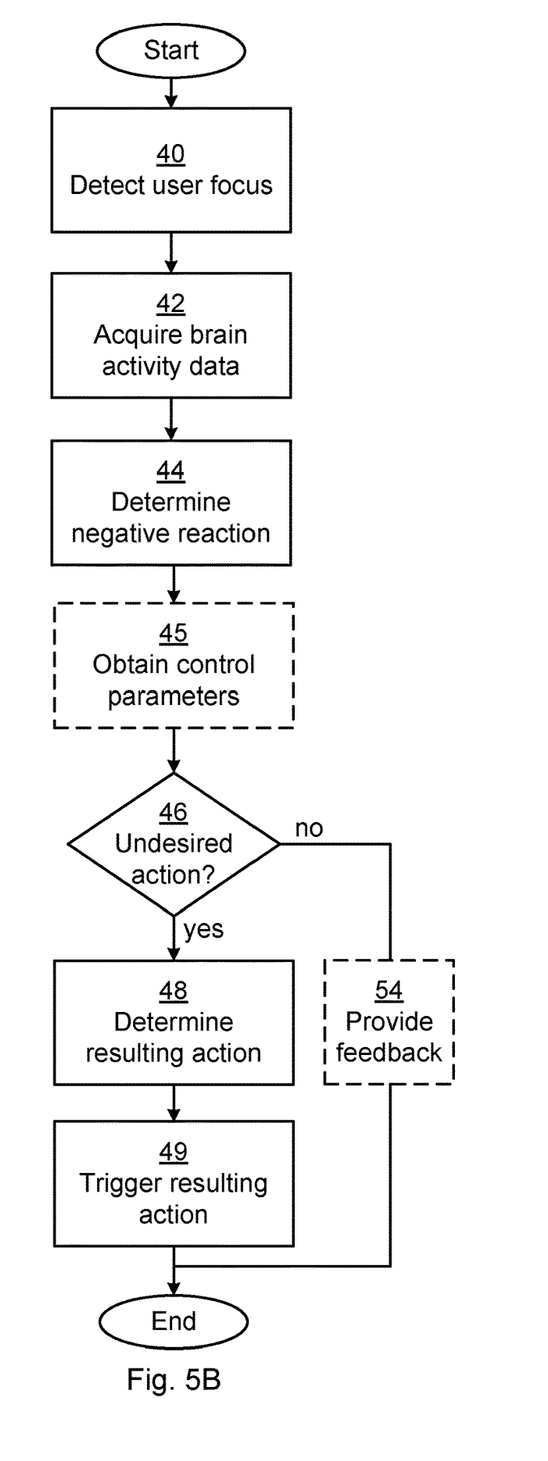
Figure 5C:
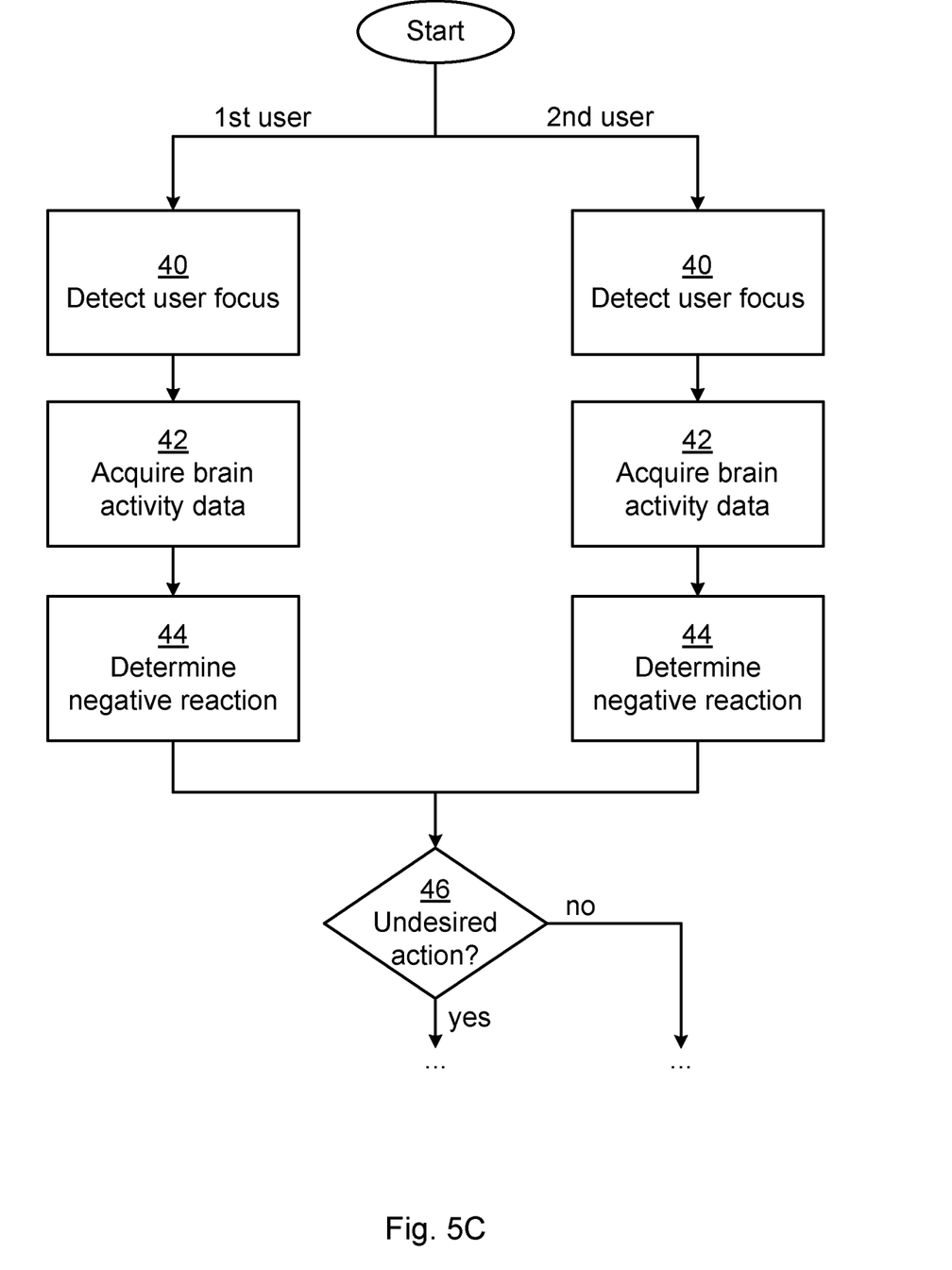

FIGS. 5A-C are flow charts illustrating methods for determining an undesired action of a first vehicle and a resulting action for an autonomous vehicle, the method being performed in the vehicle action determiner of FIG. 3. The user is travelling in the autonomous vehicle. The first vehicle can be the same as the autonomous vehicle in which the user is travelling. Alternatively, the first vehicle is external to the autonomous vehicle in which the user is travelling. The first vehicle can be an autonomous vehicle or a traditional, human controlled vehicle.

In a detect user focus step 40, the vehicle action determiner detects user focus, by detecting that a first user is focusing on a first vehicle. The term first here is only used to allow reference to the first vehicle in text below. The term first does not imply any order or priority in any way. The user focus on the first vehicle can e.g. be based on gaze tracking (using the cameras 4 shown in FIGS. 2A-B). It can also be determined when the user is focusing on its own autonomous vehicle, i.e. the autonomous vehicle in which the user is travelling.

Optionally, only vehicles within a specific distance from the first user are considered to be potential first vehicles, as vehicles far away may be difficult for the user to properly analyse.

Another camera of the vehicle where the user is located (e.g. a dashboard camera), a camera on a user device close to the user (e.g. a head mounted display used by the autonomous vehicle). Alternatively or additionally, a camera external to the vehicle can be utilised. The user eye gaze is identified in the images acquired by the cameras by knowing the relative position between the camera and the current user location, which may be known (e.g. user is sitting in the seat and has height X) or may be detected in an online manner with communication with the server 8 (e.g. another camera facing inside the car detects where the user head and eyes are located and computes the transform of position and direction between the user eyes location and the camera).

In an acquire brain activity data step 42, the vehicle action determiner acquires brain activity data of the first user. This can be performed using the brain sensor device 7 shown in FIGS. 2A-B. For instance, the brain activity data can be based on electroencephalography (EEG).

In a determine negative reaction step 44, the vehicle action determiner determines a negative reaction of the first user based on the brain activity data. As mentioned above, compared to other visionary uses of brain activity detection, the negative reaction detection is much more straightforward and feasible using data provided by the brain sensor devices available today. The determination of negative reaction can e.g. be based on machine learning.

In a conditional undesired action step 46, the vehicle action determiner determines whether the first vehicle is performing an undesired action based on the first user focusing on the first vehicle and the negative reaction of the first user. In other words, when the user is focusing on a particular vehicle and brain waves indicate that the user is having a negative reaction, this is interpreted as that the first vehicle performing an undesired action.

This determination can optionally be based on a current geographic location of the first vehicle (or the autonomous vehicle). Acceptable driving behaviour can vary significantly between different countries and this can be considered when determining whether the action is undesired or not.

Furthermore, the determination is optionally based on historic driving data of the first vehicle. For instance, if historic data indicate that many similar actions have not been associated with any undesired behaviours for tens of thousands of kilometres, this shifts the weight of the action to not be considered to be an undesired action.

When an undesired action occurs, the method proceeds to a determine resulting action step 48. Otherwise, the method ends.

In the determine resulting action step 48, the vehicle action determiner determines the resulting action to be taken by the autonomous vehicle, based on the first vehicle performing the undesired action. The resulting action can be used to train the machine learning model for the autonomous vehicle, where the inputs of the model contain one or more control parameters and the output contains the resulting action or a consequence thereof. Such training of machine learning models can be used as part of shared learning, expanding to improve the machine learning models for several vehicles. For instance, all autonomous vehicles whose owners give the permission to learn from other vehicles can learn and avoid an undesired action in a similar context in the future using such shared learning. Such shared learning can be communicated via a server or directly from the vehicle action determiner to the autonomous vehicle in question.

The resulting action can be a corrective control action of the autonomous vehicle. The corrective control action can be a real-time control action which influences behaviour of the autonomous vehicle in the current situation, which has been determined to be undesired. Such real-time corrective control action can e.g. be applied when the first vehicle (i.e. the observed vehicle) is also the vehicle which is trained. Alternatively or additionally, the corrective control action is stored in memory of the autonomous vehicle such that a corresponding undesired action can be avoided in a similar context in the future.

In one embodiment, the resulting action is that the autonomous vehicle requests additional information from a human driver to learn for a similar situation in the future. The human driver may be located inside the autonomous vehicle or remotely, to provide input to the machine learning model in the situation of the undesired action. The autonomous vehicle supplies data corresponding to the situation of the undesired action which was previously recorded. This allows the autonomous vehicle to learn how to correct such action.

In one embodiment, the resulting action is that the autonomous vehicle is mandated to receive additional training, e.g. from a simulator simulating the situation where the undesired action occurs. Optionally, this training can be triggered only when the number of such undesired actions exceeds a certain threshold. This resulting action reduces the risk that the autonomous vehicle performing the undesired action will perform such an action when a similar situation occurs in the future.

In one embodiment, the resulting action is that the autonomous vehicle requests additional information from a human driver for assistance when a similar situation as the undesired action occurs in the future. The autonomous vehicle will then ask a human driver (in the autonomous vehicle or remotely) to take over and drive the vehicle so that the autonomous vehicle can learn from the driver.

In one embodiment, the resulting action is that the autonomous vehicle is caused to perform an alternative action to the undesired action when the autonomous vehicle re-encounters the situation of the undesired action in the future. As an example, the autonomous vehicle may have two potential actions which can be performed in the situation, as action A and action B, and the autonomous vehicle will use action B if action A has been reported as undesired.

In one embodiment, the resulting action is that the autonomous vehicle accumulates the undesired action occurrences, and if the number of undesired action occurrences exceeds a given threshold, the autonomous vehicle decides to act upon the situation, either by requesting additional information, or by altering the action to be performed in the situation of the undesired action. Similarly, when the occurrences of undesired action for the action in the same situation performed by a set of autonomous vehicles accumulate to undesired action occurrences exceeding a predetermined threshold, the remaining autonomous vehicles of the same brand, owner or the autonomous vehicles in a certain geographic location also modify their action in that situation.

In one embodiment, the resulting action is that the autonomous vehicle performs at least one of the above mentioned resulting actions, weighted on the performance goals of the autonomous vehicle. As an example, it may be determined to be undesired that a vehicle has not accelerated to cross an amber traffic light before turning red. However, such acceleration would have cost the vehicle a larger energy expenditure which the vehicle has been set to optimise by the owner or by the manufacturer, or exceed a maximum acceleration limitation imposed on the vehicle by the same. Similarly, the autonomous vehicle may also want to optimise its physical conditions, such as motor condition, breaks, etc. Hence a weighted function which considers all these factors may be used when deciding if a modification of the resulting action should be performed.

When the resulting action results in the autonomous vehicle learning from the experience, the feedback of the resulting action can be shared to more autonomous vehicles to allow their respective machine learning models to be trained.

In a trigger resulting action step 49, the vehicle action determiner triggers the autonomous vehicle to perform the resulting action.

By using brain activity data, a recognition of an undesired action is achieved without the need for explicit user input. This can be used for an autonomous vehicle to learn from the undesired action. The feedback from the user can be readily correlated to the current activity being performed by the autonomous vehicle.

Embodiments presented herein allow for feedback to several autonomous vehicles and not just for the autonomous vehicle in which the user is travelling. The embodiments enable a quick and robust determination of any undesired action of vehicles. Since the feedback can occur without user interaction, large amounts of feedback data can be amassed to greatly improve the performance of the autonomous vehicles.

Looking now to FIG. 5B, only new or modified steps compared to the steps of FIG. 5A will be described.

In an optional acquire control parameters step 45, the vehicle action determiner acquires control parameters of the first vehicle.

The control parameters comprise at least one parameter describing a current motion of the first vehicle. Current motion is here to be interpreted as any one or more of velocity, acceleration, direction, etc.

Alternatively or additionally, the control parameters comprise at least one parameter relating to road characteristics of a road driven by the first vehicle. Road characteristics can e.g. not only relate to the nature of the road, such as curvature, incline, number of lanes, width, speed limit, traffic regulations, limits on acceleration/deceleration along the driving direction, lateral acceleration etc., but also to a temporary condition of the road, such as traffic conditions, road closures, amount of snow, ice or leaves and/or weather conditions such as temperature, rain, snow, sunshine and sun angle, etc. Furthermore, activity identification of the first vehicle can form part of the control parameters, such as driving straight, overtaking another vehicle and returns to original lane, driving through an amber traffic light, etc. Optionally, the control parameters also comprise information about the surroundings, e.g. other vehicles, pedestrians, bicyclists, etc., which is data that can be collected by the autonomous vehicle.

When the control parameters are available, the conditional undesired action step 46 can also be based on any one or more of the control parameters of the first vehicle.

When the control parameters are available, the determine resulting action step 48 can also be based on one or more of the control parameters of the first vehicle.

In an optional provide feedback step 54, when there is no undesired action determined in step 46, the vehicle action determiner provides feedback to the first user, indicating that the first vehicle is not performing an undesired action.

Looking now to FIG. 5C, the method illustrated here is similar to the method of FIG. 5A, but based on at least two users.

Here, steps 40, 42 and 44 are performed in two separate paths, one for a first user and one for a second user. In here, both users focus on the same first vehicle. In each instance of step 44, there is a binary classification of whether there is a negative reaction or not. The negative reaction or not is determined in each instance of step 44 as described in more detail above.

In the conditional undesired action step 46, the negative reaction and user focus from both users are used to determine whether the first vehicle is performing an undesired action.

Hence the brain activity data of at least two users are analysed, resulting in binary classifications of negative reaction or not in step 44. These binary classifications are combined in the step 46, in the determination of whether the first vehicle is performing an undesired action or not. The binary classifications can be combined in several different ways.

In one embodiment, the determination is based on an average of the binary classifications obtained from all users currently focusing on the first vehicle.

In one embodiment, the determination is based on the average of the classifications obtained from all users which are closer than a certain distance from the first vehicle and are currently focusing on the first vehicle.

In one embodiment, the determination is based on the average of the classifications obtained from users currently focusing on the first vehicles, but only those users that are locals in the current geographic area are considered. This considers cultural (e.g., Europeans vs Asians vs Americans, South Europeans vs North Europeans) and geographic interpretations of an undesired action, where a certain behaviour may be considered undesired in one country, but not in another.

In one embodiment, the determination is based on the average of the classifications obtained from all users currently focusing on the first vehicle, and also based on previous classifications of the same action which have been stored. As an example, the first vehicle might be shared among various users, where the various users have previously classified the same action which is currently being performed by the first vehicle, and the stored result is used for the determination of the undesired behaviour.

In one embodiment, the determination is based on the average of the classifications obtained from all users currently focusing on the first vehicle, and also based on previous knowledge from the first vehicle about the action. The previous knowledge about the action can e.g. be obtained by previous training (real or simulation of human driver), and/or the driver's manual. As an example, the first vehicle may have a strong belief that such action is not undesired due to previous knowledge.

In one embodiment, the determination is based on the average of the classifications obtained from all users focusing on the first vehicle, as well as the road regulations which can be retrieved from the driving code regulations.

Hence, given the EEG recordings from at least two users, the current action being performed by multiple vehicles is classified as undesired. As an example, if multiple vehicles are involved in an undesired action (e.g. users which focus on both vehicle A and vehicle B report undesired actions), the undesired action may not be trivially assigned to a specific vehicle. Hence, the classification from multiple users must be considered. As an example, consider that vehicle A and B are involved in an undesired action. The classifications from users which focus on vehicle A or vehicle B are considered, for example, to distinguish if a larger number of undesired classifications allocated to vehicle A than vehicle B, or vice versa. This embodiment could be implemented on the server (8 of FIG. 3 and FIG. 4C).

After step 46, the method performs in an analogous way to what is illustrated in FIGS. 5A and 5B.

Figure 6:
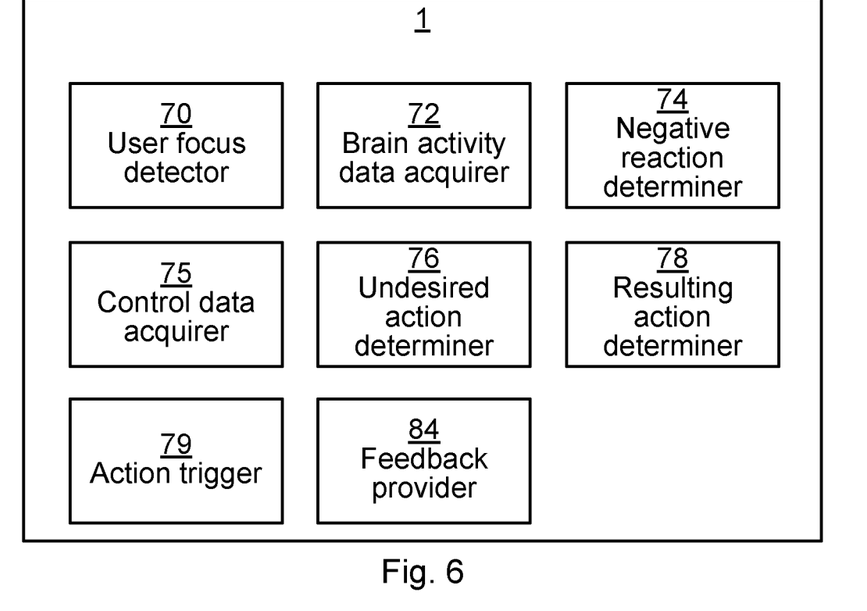
FIG. 6 is a schematic diagram showing functional modules of the vehicle action determiner of FIG. 3 according to one embodiment.

FIG. 6 is a schematic diagram showing functional modules of the vehicle action determiner 1 of FIG. 3 according to one embodiment. The modules are implemented using software instructions such as a computer program executing in the vehicle action determiner 1. Alternatively or additionally, the modules are implemented using hardware, such as any one or more of an ASIC (Application Specific Integrated Circuit), an FPGA (Field Programmable Gate Array), or discrete logical circuits. The modules correspond to the steps in the methods illustrated in FIGS. 5A-5C.

A user focus detector 70 corresponds to step 40. A brain activity data acquirer 72 corresponds to step 42. A negative reaction determiner 74 corresponds to step 44. A control data acquirer m corresponds to step 45. An undesired action determiner 76 corresponds to step 46. A resulting action determiner 78 corresponds to step 48. An action trigger 79 corresponds to step 49. A feedback provider 84 corresponds to step 54.

Figure 7:
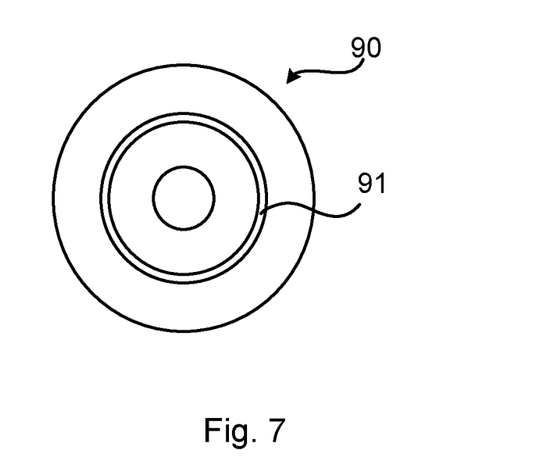
FIG. 7 shows one example of a computer program product comprising computer readable means.

FIG. 7 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 67 of FIG. 3. While the computer program 91 is here schematically shown as a track on the depicted optical disk, the computer program can be stored in any way which is suitable for the computer program product, such as a removable solid state memory, e.g. a Universal Serial Bus (USB) drive.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for determining an undesired action of a first vehicle and a resulting action, the method being performed in a vehicle action determiner and comprising the steps of:
   detecting user focus, by detecting that a first user is focusing on the first vehicle;
   determining a distance to the first vehicle;
   acquiring brain activity data of the first user, wherein the brain activity data is based on an electroencephalography measurement;
   determining a negative reaction of the first user based on the brain activity data;
   determining when the first vehicle is performing an undesired action based on the first user focusing on the first vehicle and the negative reaction of the first user;
   determining the resulting action to be taken by an autonomous vehicle, based on the first vehicle performing the undesired action and the distance to the first vehicle being less than a predefined distance; and
   triggering the autonomous vehicle to perform the resulting action.

2. The method according to claim 1, wherein the steps of detecting user focus, acquiring brain activity data are repeated for a second user and wherein the step of determining when the first vehicle is performing an undesired action is further based on the second user focusing on the first vehicle and a negative reaction of the second user.

3. The method according to claim 1, further comprising the step of:
   acquiring control parameters of the first vehicle; and
   wherein the step of determining when the first vehicle is performing an undesired action is further based on the control parameters of the first vehicle.

4. The method according to claim 3, wherein the control parameters comprise at least one parameter describing a current motion of the first vehicle.

5. The method according to claim 3, wherein the control parameters comprise at least one parameter relating to road characteristics of a road driven by the first vehicle.

6. The method according to claim 3, wherein the step of determining a resulting action comprises considering control parameters of the first vehicle.

7. The method according to claim 1, wherein the step of detecting user focus is based on gaze tracking.

8. A vehicle action determiner for determining an undesired action of a first vehicle and a resulting action, the vehicle action determiner comprising:
a processor; and
a memory storing instructions that, when executed by the processor, cause the vehicle action determiner to:
detect user focus, by detecting that a first user is focusing on the first vehicle;
determining a distance to the first vehicle;
acquire brain activity data of the first user, wherein the brain activity data is based on an electroencephalography measurement;
determine a negative reaction of the first user based on the brain activity data;
determine when the first vehicle is performing an undesired action based on the first user focusing on the first vehicle and the negative reaction of the first user;
determine the resulting action to be taken by an autonomous vehicle, based on the first vehicle performing the undesired action and the distance to the first vehicle being less than a predefined distance; and
trigger the autonomous vehicle to perform the resulting action.

9. The vehicle action determiner according to claim 8, wherein the instructions to detect user focus, and to acquire brain activity data are repeated for a second user and wherein the instructions to determine when the first vehicle is performing an undesired action is further based on the second user focusing on the first vehicle and a negative reaction of the second user.

10. The vehicle action determiner according to claim 8, further comprising instructions that, when executed by the processor, cause the vehicle action determiner to:
acquire control parameters of the first vehicle; and
wherein the instructions to determine when the first vehicle is performing an undesired action is further based on the control parameters of the first vehicle.

11. The vehicle action determiner according to claim 10, wherein the control parameters comprise at least one parameter describing a current motion of the first vehicle.

12. The vehicle action determiner according to claim 10, wherein the control parameters comprise at least one parameter relating to road characteristics of a road driven by the first vehicle.

13. The vehicle action determiner according to claim 10, wherein the instructions to determine a resulting action comprise instructions that, when executed by the processor, cause the vehicle action determiner to consider control parameters of the first vehicle.

14. The vehicle action determiner according to claim 8 wherein the instructions to detect comprise instructions that, when executed by the processor, cause the vehicle action determiner to detect user focus based on gaze tracking.

15. The vehicle action determiner according to claim 8, wherein the instructions to determine when the first vehicle is performing an undesired action comprise instructions that, when executed by the processor, cause the vehicle action determiner to determine that the first vehicle is performing an undesired action further based on a current geographic location of the first vehicle.

16. The vehicle action determiner according to claim 8, wherein the instructions to determine when the first vehicle is performing an undesired action comprise instructions that, when executed by the processor, cause the vehicle action determiner to determine when the first vehicle is performing an undesired action further based on historic driving data of the first vehicle.

17. The vehicle action determiner according to claim 8, wherein in the instructions to determine a resulting action, the resulting action is a corrective control action of the autonomous vehicle.

18. The vehicle action determiner according to claim 8, further comprising instructions that, when executed by the processor, cause the vehicle action determiner to provide, when the first vehicle is not performing an undesired action, feedback to the first user, indicating that the first vehicle is not performing an undesired action.

19. A non-transitory computer-readable medium comprising a computer program for determining an undesired action of a first vehicle and a resulting action that when executed by a processor of a vehicle action determiner cause, the computer program comprising computer program code which, when run on a vehicle action determiner causes the vehicle action determiner to:
detect user focus, by detecting that a first user is focusing on the first vehicle;
determining a distance to the first vehicle;
acquire brain activity data of the first user, wherein the brain activity data is based on an electroencephalography measurement;
determine a negative reaction of the first user based on the brain activity data; and
determine when the first vehicle is performing an undesired action based on the first user focusing on the first vehicle and the negative reaction of the first user and the distance to the first vehicle being less than a predefined distance.

* * * * *

UNITED STATES PATENT AND TRADEMARK OFFICE
CERTIFICATE OF CORRECTION

PATENT NO. : 11,634,159 B2
APPLICATION NO. : 16/769730
DATED : April 25, 2023
INVENTOR(S) : Araújo et al.

It is certified that error appears in the above-identified patent and that said Letters Patent is hereby corrected as shown below:

In the Specification

In Column 4, Line 52, delete "a mass" and insert -- amass --, therefor.

In Column 5, Line 11, delete "a mass" and insert -- amass --, therefor.

In Column 5, Line 29, delete "2C" and insert -- 2c --, therefor.

In Column 7, Line 13, delete "undesired" and insert -- undesired action --, therefor.

In Column 7, Line 24, delete "undesired" and insert -- undesired action --, therefor.

In Column 10, Line 34, delete "returns" and insert -- returning --, therefor.

In Column 11, Line 54, delete "allocated" and insert -- are allocated --, therefor.

In Column 12, Line 6, delete "m" and insert -- 75 --, therefor.

In the Claims

In Column 14, Lines 37-39, in Claim 19, delete "cause, the computer program comprising computer program code which, when run on a vehicle action determiner causes" and insert -- cause --, therefor.

Signed and Sealed this
Sixteenth Day of April, 2024

Katherine Kelly Vidal
*Director of the United States Patent and Trademark Office*